US010893815B2

(12) United States Patent
Pande et al.

(10) Patent No.: US 10,893,815 B2
(45) Date of Patent: Jan. 19, 2021

(54) HEART RATE MEASUREMENT AND A PHOTOPLETHYSMOGRAPH (PPG) HEART RATE MONITOR

(71) Applicant: Texas Instruments Incorporated, Dallas, TX (US)

(72) Inventors: Tarkesh Pande, Richardson, TX (US); David Patrick Magee, Allen, TX (US)

(73) Assignee: Texas Instruments Incorporated, Dallas, TX (US)

( * ) Notice: Subject to any disclaimer, the term of this patent is extended or adjusted under 35 U.S.C. 154(b) by 24 days.

(21) Appl. No.: 16/271,246

(22) Filed: Feb. 8, 2019

(65) Prior Publication Data

US 2019/0167129 A1 Jun. 6, 2019

Related U.S. Application Data

(62) Division of application No. 14/970,434, filed on Dec. 15, 2015, now abandoned.

(51) Int. Cl.
*A61B 5/024* (2006.01)
*A61B 5/00* (2006.01)

(52) U.S. Cl.
CPC ........ *A61B 5/02416* (2013.01); *A61B 5/0002* (2013.01); *A61B 5/721* (2013.01);
(Continued)

(58) Field of Classification Search
CPC .................................................... A61B 5/721
See application file for complete search history.

(56) References Cited

U.S. PATENT DOCUMENTS

2008/0152161 A1  6/2008  Kim
2009/0156948 A1*  6/2009  Shimizu ............... A61B 5/7207
                                                                600/509
(Continued)

OTHER PUBLICATIONS

Alrick B. Hertzman, "The Blood Supply of Various Skin Areas as Estimated by the Photoelectric Plethysmograph", American Journal of Physiology, vol. 124, Issue 2, 1938, pp. 328-340.
Simon Haykin, "Adaptive Filter Theory", Pearson Education, Inc., 2002, pp. 320-323 and 443.
(Continued)

*Primary Examiner* — Rex R Holmes
*Assistant Examiner* — Jennifer L Ghand
(74) *Attorney, Agent, or Firm* — Lawrence J. Bassuk; Charles A. Brill; Frank D. Cimino (57) ABSTRACT

A method for heart rate measurement in a photoplethysmograph (PPG) heart rate monitor device is provided that includes performing motion compensation on a PPG signal wherein a motion compensated PPG signal $PPG_{accX}$ is generated with reference to an X-axis acceleration signal, a motion compensated PPG signal $PPG_{accY}$ is generated with reference to a Y-axis acceleration signal, and a motion compensated PPG signal $PPG_{accZ}$ is generated with reference to a Z-axis acceleration signal, combining $PPG_{accX}$, $PPG_{accY}$, and $PPG_{accZ}$ to generate a final motion compensated PPG signal, wherein a first weight is applied $PPG_{accX}$, a second weight is applied to $PPG_{accY}$, and a third weight is applied to $PPG_{accZ}$, performing a single Fourier Transform (FT) on the final motion compensated PPG signal to generate a frequency domain PPG signal; and estimating a heart rate based on the frequency domain PPG signal.

16 Claims, 5 Drawing Sheets

(52) U.S. Cl.
CPC .............. *A61B 5/725* (2013.01); *A61B 5/7246* (2013.01); *A61B 5/7257* (2013.01)

(56) References Cited

U.S. PATENT DOCUMENTS

| | | | |
|---|---|---|---|
| 2010/0298656 A1* | 11/2010 | McCombie | A61B 5/1114 600/301 |
| 2012/0203080 A1 | 8/2012 | Kim | |
| 2012/0220881 A1* | 8/2012 | Takahashi | A61B 5/7207 600/483 |
| 2015/0351646 A1 | 12/2015 | Cervini | |
| 2016/0022220 A1* | 1/2016 | Lee | A61B 5/02433 600/479 |
| 2016/0051157 A1 | 2/2016 | Waydo | |
| 2016/0317097 A1* | 11/2016 | Adams | A61B 5/725 |
| 2017/0143274 A1* | 5/2017 | Pande | A61B 5/7225 |
| 2019/0192082 A1* | 6/2019 | Shin | A61B 5/7225 |

OTHER PUBLICATIONS

Zhilin Zhang et al, "TROIKA: A General Framework for Heart Rate Monitoring Using Wrist-Type Photoplethysmographic Signals During Intensive Physical Exercise", IEEE Transactions on Biomedical Engineering, vol. 62, No. 2, Feb. 2015, pp. 522-531.

Ralph W.C.G.R. Wijshoff et al,"Reducing Motion Artifacts in Photoplethysmograms by Using Relative Sensor Motion: Phantom Study", Journal of Biomedical Optics, vol. 17, No. 11, Nov. 2012, pp. 117007-1-117007-15.

Tim Schack et al, "A New Method for Heart Rate Monitoring During Physical Exercise using Photoplethysmographic Signals", 23rd European Signal Processing Conference, Nice, France, Feb. 25, 2015, pp. 2716-2720.

Hayato Fukushima et al, "Estimating Heart Rate using Wrist-type Photoplethysmography and Acceleration Sensor While Running", 34th Annual International Conference of the IEEE EMBS, Aug. 28-Sep. 1, 2012, San Diego, CA, pp. 2901-2904.

* cited by examiner

HEART RATE MEASUREMENT AND A PHOTOPLETHYSMOGRAPH (PPG) HEART RATE MONITOR

This application is a Divisional of prior application Ser. No. 14/970,434, filed Dec. 15, 2015, now abandoned.

BACKGROUND OF THE DISCLOSURE

Field of the Invention

Embodiments of the present invention generally relate to heart rate measurement and more specifically relate to reducing motion induced artifacts in photoplethysomography (PPG) signals used for heart rate measurement.

Description of the Related Art

Photoplethysmography (PPG) is a well-known optical method for measuring the change in blood flow. In PPG, a light source at a particular wavelength, typically, red, infrared or green, is kept at a skin surface and the reflected light is measured and related to blood flow. The change in blood flow can be used to compute vital statistics such as heart rate, respiration rate and other health related statistics. Many consumer fitness devices use PPG to estimate the heart rate of the person wearing the device. PPG based heart rate estimation during motion can be adversely affected by motion artifacts in the PPG signal. The motion artifacts may be caused by, for example, hemodynamic effects, tissue deformation, and sensor movement relative to the skin.

SUMMARY

Embodiments of the present invention relate to methods, apparatus, and computer readable media for reducing motion induced artifacts in photoplethysomography (PPG) signals used for heart rate measurement. In one aspect, a method for heart rate measurement in a photoplethysmograph (PPG) heart rate monitor device is provided that includes receiving a PPG signal from a PPG sensor of the heart rate monitor device, receiving an X-axis acceleration signal, a Y-axis acceleration signal, and a Z-axis acceleration signal from an accelerometer of the heart rate monitor device, performing motion compensation on the PPG signal, wherein a first motion compensated PPG signal is generated with reference to the X-axis acceleration signal, a second motion compensated PPG signal is generated with reference to the Y-axis acceleration signal, and a third motion compensated PPG signal is generated with reference to the Z-axis acceleration signal, combining the first motion compensated PPG signal, the second motion compensated PPG signal, and the third motion compensated PPG signal to generate a fourth motion compensated PPG signal, wherein a first weight is applied to the first motion compensated PPG, a second weight is applied to the second motion compensated PPG signal, and a third weight is applied to the third motion compensated PPG signal, performing a single Fourier Transform (FT) on the fourth motion compensated PPG signal to generate a frequency domain PPG signal, and estimating a heart rate based on the frequency domain PPG signal.

In one aspect, a photoplethysmograph (PPG) heart rate monitor device is provided that includes a PPG sensor component configured to generate an analog PPG signal, an accelerometer configured to generate an X-axis acceleration signal, a Y-axis acceleration signal, and a Z-axis acceleration signal, a motion compensation component coupled to the PPG sensor to receive the PPG signal and coupled to the accelerometer to receive the X-axis acceleration signal, the Y-axis acceleration signal, and the Z-axis acceleration signal, wherein the motion compensation component is configured to generate a first motion compensated PPG signal with reference to the X-axis acceleration signal, a second motion compensated PPG signal with reference to the Y-axis acceleration signal, and a third motion compensated PPG signal with reference to the Z-axis acceleration signal, a combiner configured to combine the first motion compensated PPG signal, the second motion compensated PPG signal, and the third motion compensated PPG signal to generate a fourth motion compensated PPG signal, wherein a first weight is applied to the first motion compensated PPG, a second weight is applied to the second motion compensated PPG signal, and a third weight is applied to the third motion compensated PPG signal, a FT component configured to perform a single Fast Fourier Transform (FFT) on the fourth motion compensated PPG signal to generate a frequency domain PPG signal, and a heart rate tracker component configured to estimate a heart based on the frequency domain PPG signal.

BRIEF DESCRIPTION OF THE DRAWINGS

Particular embodiments will now be described, by way of example only, and with reference to the accompanying drawings.

DETAILED DESCRIPTION OF EMBODIMENTS OF THE DISCLOSURE

Specific embodiments of the invention will now be described in detail with reference to the accompanying figures. Like elements in the various figures are denoted by like reference numerals for consistency.

As previously mentioned, motion artifacts in a PPG signal can adversely affect heart rate estimation. Some current approaches to improving heart rate estimation when motion artifacts may be present in the PPG signal attempt to remove the motion component in the PPG signal using information from an external signal reference such as an accelerometer. For example, in H. Fukushima, et al., "Estimating Heart Rate using Wrist-Type Photoplethysmography and Acceleration Sensor While Running," 34th Annual Internal Conference of the IEEE Engineering in Medicine and Biology Society, pp. 2901-2904, Aug. 28-Sep. 1, 2012, a spectrum subtraction technique is proposed that removes the spectrum of the acceleration data from that of the PPG signal prior to heart rate estimation.

In another example, in Z. Zhang, et al., "TROIKA: A General Framework for Heart Rate Monitoring using Wrist-type Photoplethysmographic Signals During Intensive Physical Exercise," IEEE Transactions on Biomedical Engineering, Vol. 62, No. 2, pp. 522-531, February, 2015, an algorithm that uses compressed sensing techniques combined with signal decomposition for de-noising and spectral tracking is proposed. The algorithm was applied to data collected from twelve different individuals carrying out a set of activities. The mean error in beats per minute (BPM) across all data sets was found to be 2.34 BPM. This technique was later improved upon in T. Schack, et al., "A New Method for Heart Rate Monitoring During Physical Exercise using Photoplethysmographic Signals," 23$^{rd}$ European Signal Processing Conference (EUSIPCO), pp. 2716-2720, Aug. 31-Sep. 4, 2015 ("Schack" herein). In the improved technique, the PPG signal is cleaned up using a normalized least mean squares (NLMS) filter and is non-coherently combined. Applying the algorithm to the twelve data sets resulted in a mean error of 1.77 BPM. As is described in more detail below, this algorithm requires three Fast Fourier Transforms (FFT) which may not be suitable for embedded applications.

Figure 1:
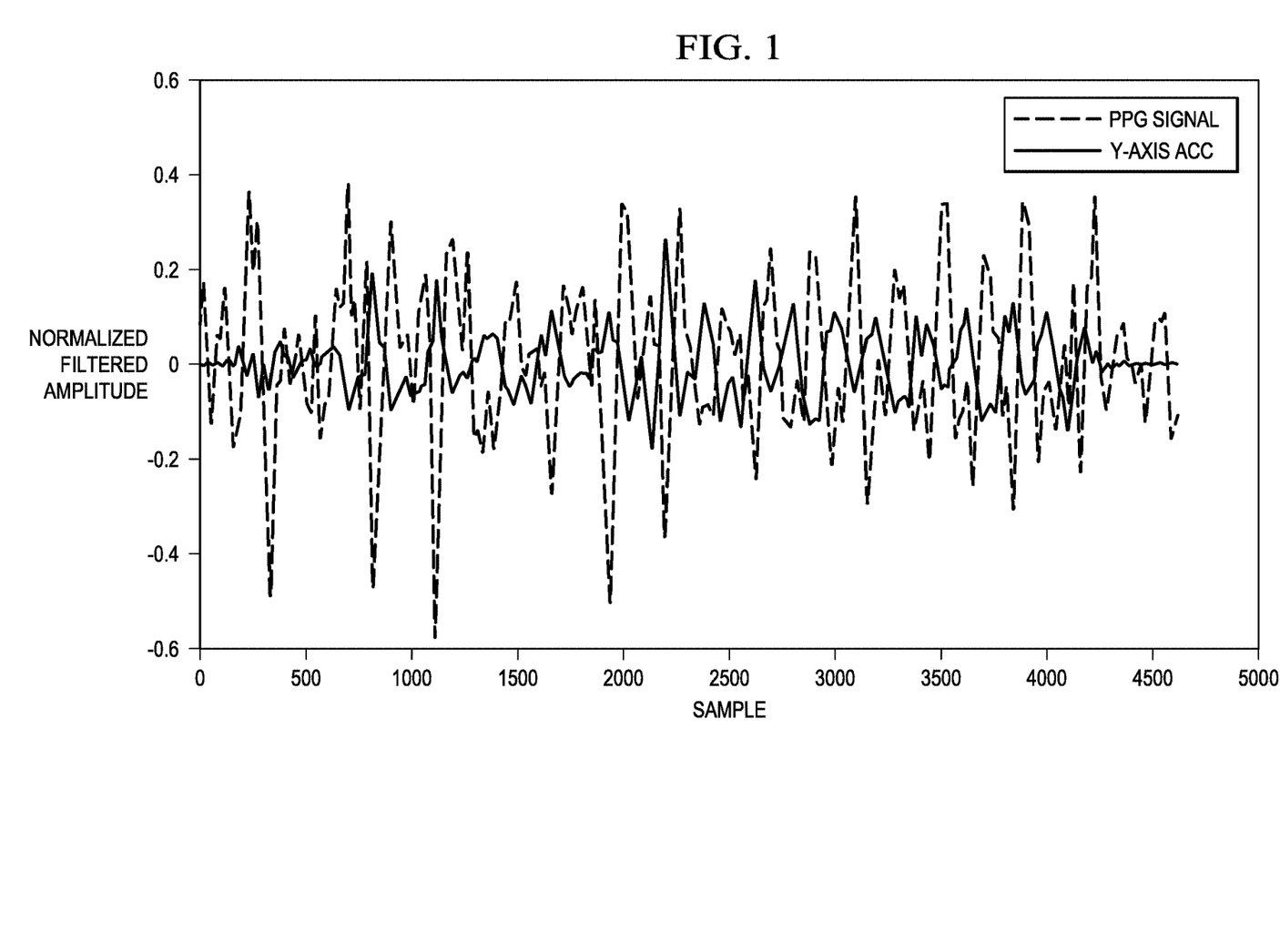
FIG. 1 and FIG. 2 are graphs.

The inherent assumption in accelerometry based cancellation of motion artifacts such the previously described algorithms is that the motion induced artifacts in the PPG signal are highly correlated with the acceleration signal. FIG. 1 is a graph illustrating this assumption with data from a wrist worn device with a PPG sensor and a three-axis accelerometer sensor in which the hand motion is performed in the direction of the Y-axis of the accelerometer. This graph shows that the Y-axis acceleration signal is inversely proportional to the PPG signal when there is motion in the Y-axis. This observation motivates the use of an interference cancellation procedure such as an NLMS filter to remove the motion component from the PPG signal.

Figure 2:
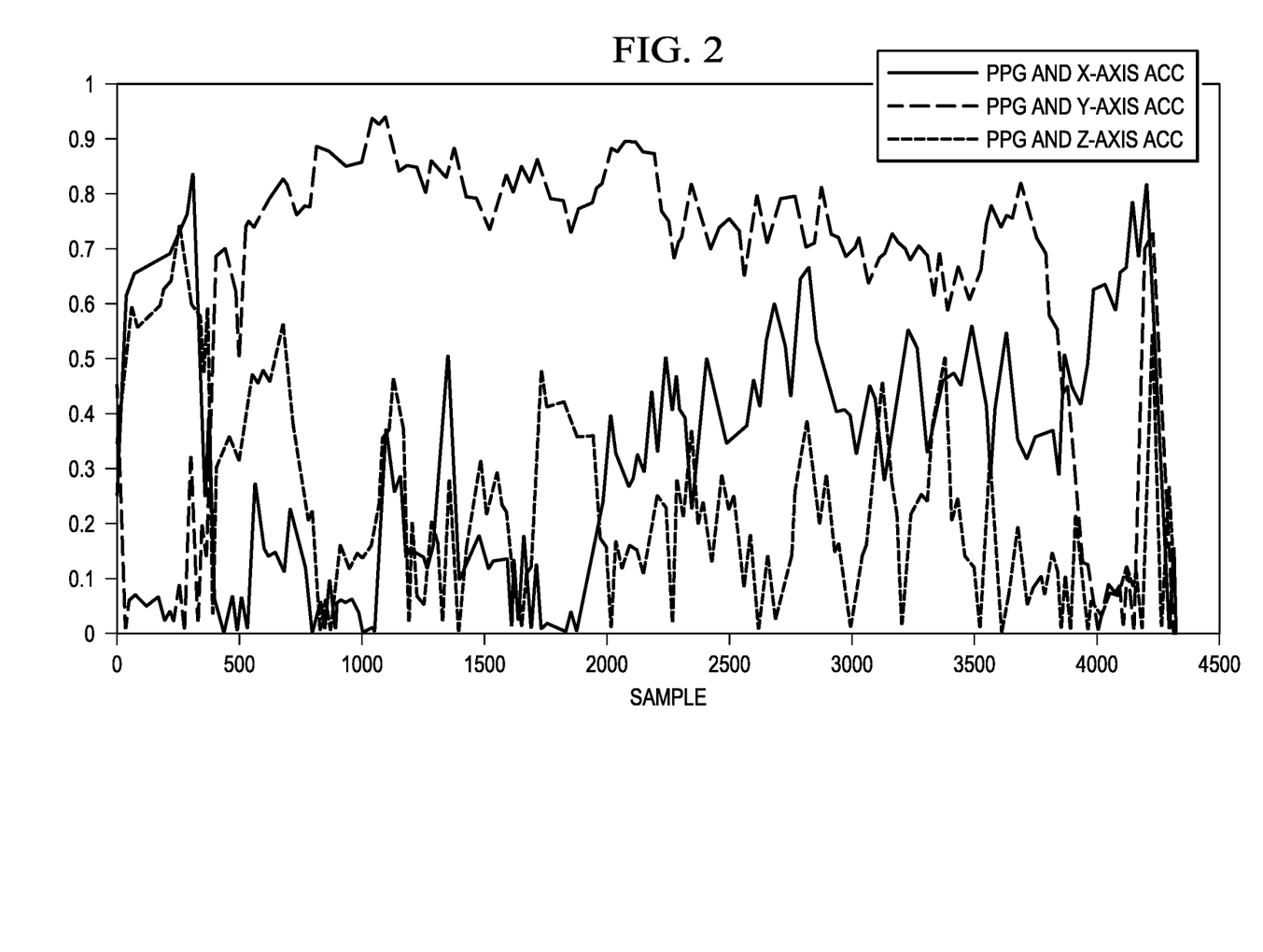

The amount of mutual information between a PPG signal and an accelerometer signal can, in a first order approximation, be captured by computing the Pearson correlation coefficient defined as $$r = \frac{\text{cov}(ppg, acc)}{\sigma_{acc}\sigma_{ppg}}$$

where cov(ppg,acc) denotes the covariance between the PPG signal and the accelerometer signal over a window of time of length T, $\sigma_{acc}$ is the standard deviation of the accelerometer signal over the same window length of time T and, $\sigma_{ppg}$ is the standard deviation of the PPG signal over a window of time of length T. FIG. 2 is a graph illustrating the Pearson correlation for the X-axis acceleration signal (accX), the Y-axis acceleration signal (accY) and the z-axis acceleration signal (accZ) of an accelerometer with respect to the PPG signal when the motion is predominantly along the Y-axis. In this graph, the Pearson correlation coefficient associated with the Y-axis acceleration signal is consistently larger than that associated with the X-axis and Z-axis as the motion of the hand is predominantly in the direction of the Y-axis.

In normal human movement, the motion occurs in all three axes. Thus, the motion interference cancellation should be done with respect to inputs from all three accelerometer axis signals. In Schack, the motion filtered PPG outputs with respect to accX, accY, and accZ are non-coherently combined and the heart rate is computed with respect to the resulting spectrum. The algorithm of Schack can be written as $$S(f) = \sqrt[3]{|\text{FFT}(\text{PPG}_{accX})|^2 \times |\text{FFT}(\text{PPG}_{accY})|^2 \times |\text{FFT}(\text{PPG}_{accZ})|^2}$$

Heart Rate=HeartRateTracker($S(f)$)

where $S(f)$ is the non-coherent power spectrum, HeartRateTracker computes the heart rate from the power spectrum, $\text{PPG}_{accX}$ is the NLMS filter output with an input of the PPG signal with the accX signal as the reference signal, $\text{PPG}_{accY}$ is the NLMS filter output with an input of the PPG signal with the accY signal as the reference signal, and $\text{PPG}_{accZ}$ is the NLMS filter output with an input of the PPG signal with the accZ signal as the reference signal. A simple version of HeartRateTracker associates the heart rate with the frequency index of the largest spectrum peak in $S(f)$.

Embodiments of the disclosure provide for reducing motion induced artifacts in PPG signals with reduced complexity and improved performance over the prior art. As is described in more detail herein, in some embodiments, instead of requiring three FFTs with non-coherent averaging as in Schack, coherent combining of NLMS filter outputs (or other suitable adaptive filter outputs) is performed followed by a single Fourier Transform (FT). The resulting signal can then be used for heart rate estimation. Experiments have demonstrated a mean error of at least 1.27 BPM.

In embodiments of the disclosure, the motion compensated power spectrum of the PPG signal may be computed as $$S(f) = |\text{FFT}(a \cdot \text{PPG}_{accX} + b \cdot \text{PPG}_{accY} + c \cdot \text{PPG}_{accZ})|^2$$

where a, b, and c are weights applied to the outputs of suitable adaptive filters. Embodiments are described herein assuming the adaptive filters are NLMS filters. One of ordinary skill in the art will understand embodiments in which other adaptive filters are used, such as, for example recursive least squares (RLS) filters. NLMS filters are described in S. Haykin, "Adaptive Filter Theory", pp. 320-324, Pearson Education, Inc., 2002, which is incorporated by reference herein. RLS filters are described in Haykin, p. 443, which is incorporated by reference herein. Any suitable technique for determining the weight values of the power spectrum computation may be used. Some examples of suitable techniques are now described.

In some embodiments, the weights are all the same value, i.e., a=b=c=K where K is a constant. This equal weighting may be used, for example, to simplify implementation. The choice of K is implementation dependent. In some embodiments, K=1 such that the three NLMS output signals are added without weighting.

In some embodiments, the values of the weights are based on the amount of correlation of the PPG signal with the respective acceleration signals. The weighting is based on the idea that the higher the correlation of the PPG signal with the corresponding acceleration signal, the more motion compensated the output of the corresponding NLMS filter should be. To determine the weight values, the correlation coefficients between each acceleration signal and the PPG signal are computed in a T second window and the weights are then computed as a function of the correlation coefficients. In one embodiment, the maximum correlation coefficients are used.

For example, if there are m samples in a T second window, the correlation $r_{1accX}$ between the accX signal and the PPG signal at time n+m/2 can be computed as $$\mu_{accX} = \frac{1}{m}\sum_{k=n}^{n+m-1} accX(k)$$

-continued $$\mu_{PPG} = \frac{1}{m}\sum_{k=n}^{n+m-1} PPG(k)$$

$$r_{1accX}(n+m/2) = \frac{\sum_{k=n}^{n+m-1}(accX(k)-\mu_{accX})(PPG(k)-\mu_{PPG})}{\sqrt{\sum_{k=n}^{n+m-1}accX(k)}\sqrt{\sum_{k=n}^{n+m-1}PPG(k)}}.$$

The maximum of the correlation coefficients in the T second window may be computed as $$r_{accX}=\max(r_{1accX}(n) \ldots r_{1accX}(n+m-1)).$$

The maximum of the correlation coefficients between the accY signal and the PPG signal, $r_{accY}$, and between the accZ signal and the PPG signal, $r_{accX}$, may be similarly computed. The weight values may then be determined as a function of $r_{accX}$, $r_{accY}$, and $r_{accZ}$. For example, in one embodiment, the weight values may be determined as $$a = \frac{r_{accX}}{r_{accX}+r_{accY}+r_{accZ}}; b = \frac{r_{accY}}{r_{accX}+r_{accY}+r_{accZ}};$$

$$c = \frac{r_{accZ}}{r_{accX}+r_{accY}+r_{accZ}}.$$

The value of T is typically chosen to be the size of the data over which the FT is performed and is of the order of a few seconds.

In some embodiments, the values of the weights are based on the predicted motion artifact energy, i.e., interference energy, removed by the NLMS filter over a window of T seconds. The NLMS filter output at time n when the sensor reference is the X-axis acceleration signal is given by $$PPG_{accX}(n)=PPG(n)-\text{Interf}_{accX}(n),$$

where PPG(n) is the PPG signal at time n and $\text{Interf}_{accX}$(n) is the interference energy removed, which is given by $$\text{Interf}_{accX}(n) = \sum_{k=1}^{N} accX(n-k)*w(n-k)$$

where w denotes the NLMS filter coefficients for accX, and [$acc_X$(n-1), . . . ,$acc_X$(n-N)] denotes the accX measurements.

The predicted interference energy removed over a window of T seconds (Tsec) by the NLMS filter corresponding to accX may thus be determined as per $$IntEn_{accX} = \sum_{Tsec} |\text{Interf}_{accX}(n)|^2.$$

The predicted interference energy corresponding to accY, $IntEn_{accY}$, and accZ, $IntEn_{accZ}$, may be similarly determined. The values of the weights may then be determined as a function of $IntEn_{accX}$, $IntEn_{accY}$, and $IntEn_{accY}$. For example, in one embodiment, the weight values may be determined as $$a = \frac{IntEn_{accX}}{IntEn_{accX}+IntEn_{accY}+IntEn_{accZ}};$$

$$b = \frac{IntEn_{accY}}{IntEn_{accX}+IntEn_{accY}+IntEn_{accZ}};$$

$$c = \frac{IntEn_{accZ}}{IntEn_{accX}+IntEn_{accY}+IntEn_{accZ}}.$$

The value of T is typically chosen to be the size of the data over which the FT is performed and is of the order of a few seconds.

In some embodiments, rather than combining all the signals output by the NLMS filters to generate the signal used for heart rate estimation, one of the signals is selected according to some suitable selection criteria. One selection criteria may be to select one of the output signals based on the maximum correlation between the PPG signal and the reference acceleration signal. More specifically, the output signal with the maximum correlation may be given a weight of 1 while the other output signals may be given a 0 weight. For example, if $r_{accY}$ is the maximum correlation, then a=0, b=1, and c=0 and $$S(f)=|FFT(0*PPG_{accX}+1*PPG_{accY}+0*PPG_{accZ})|^2=|FFT(PPG_{accY})|^2.$$

The decision rules may be written as if $r_{accX}=\max(r_{accX},r_{accY},r_{accZ})$ $a=1;b=0;c=0$ if $r_{accY}=\max(r_{accX},r_{accY},r_{accZ})$ $a=0;b=1;c=0.$ if $r_{accZ}=\max(r_{accX},r_{accY},r_{accZ})$ $a=0;b=0;c=1$ Another selection criteria may be to select one of the output signals having the maximum interference energy removed. More specifically, the output signal with the maximum interference energy removed may be given a weight of 1 while the other output signals may be given a 0 weight. For example, if $IntEn_{accY}$ has the maximum interference energy removed, then a=0, b=1, and c=0 and $$S(f)=|FFT(0*PPG_{accX}+1*PPG_{accY}+0*PPG_{accZ})|^2=|FFT(PPG_{accY})|^2.$$

The decision rules may be written as if $IntEn_{accX}=\max(IntEn_{accX},IntEn_{accY},IntEn_{accZ})$ $a=1;b=0;c=0$ if $IntEn_{accY}=\max(IntEn_{accX},IntEn_{accY},IntEn_{accZ})$ $a=0;b=1;c=0.$ if $IntEn_{accZ}=\max(IntEn_{accX},IntEn_{accY},IntEn_{accZ})$ $a=0;b=0;c=1$ In some embodiments, rather than constantly filtering the PPG signal to compensate for motion artifacts, the PPG signal is filtered when the user of the device is in motion and not filtered otherwise. Filtering the PPG signal to remove motion artifacts when the user of the device is not in motion may degrade the PPG signal as motion artifacts are not present. Any suitable technique may be used to determine if the user is in motion. As shown in Table 1, one suitable technique that may be used is to compute the variance of the sum of squares of the acceleration signals over a window of T1 seconds having m1 samples and compare the variance to a predetermined threshold Thresh. If the variance exceeds the threshold, the user is determined to be in motion at time instant n; otherwise the user is determined to be stationary. Any suitable threshold value may be used. In some embodiments, the threshold value is determined empirically based on experiments performed on the acceleration signals to determine a good representation of stationary.

TABLE 1

Let
$$accsq(n) = accX\,(n)^2 + accY\,(n)^2 + accZ\,(n)^2$$

$$\mu_{accVar}(n) = \frac{1}{m1} \sum_{k=n}^{n+m1-1} accsq(k)$$

Figure 3:
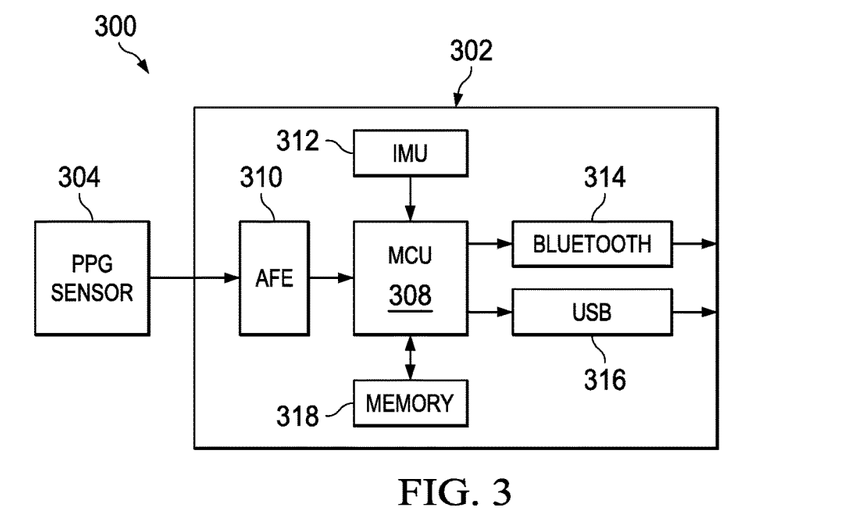
FIG. 3 is a block diagram of an example photoplethysmograph (PPG) heart rate monitor device.

Then, $$accVar(n) = \frac{1}{m1-1} \sum_{k=n}^{n+m1-1} (accsq(k) - \mu_{accVar}(n))^2$$

if
   $accVar(n) < Thresh\,-\,>$ stationary
elseif
   $accVar(n) \geq Thresh\,-\,>$ motion FIG. 3 is a block diagram of an example embedded photoplethysmograph (PPG) heart rate monitor device 300 configured to perform motion compensation on PPG signals as described herein. The PPG heart rate monitor device 300 includes a PPG sensor component 304 configured to capture a PPG signal from the person wearing the monitor device 300 and a processing component 302 configured to process the PPG signal to measure the heart rate of a person wearing the monitor device.

The PPG sensor component 304 may be any suitable PPG sensor. In general, the PPG sensor component includes one or more three light emitting diodes (LEDs) and a photodiode arranged to the wavelengths of the light from the one or more LEDs. In some embodiments, the PPG sensor component 304 includes three light emitting diodes (LEDs): a green light emitting diode (LED), a red LED, and an infrared LED.

The processing component 302 includes a microcontroller (MCU) 308, an inertial measurement unit (IMU) 312, a Bluetooth transceiver 314, an analog front end (AFE) 310, and memory 318. The MCU 308 may be any suitable microcontroller, such as, for example, an MSP430 device available from Texas Instruments, Inc. The MCU 308 includes memory (one example of a computer readable medium) that can be used to store software instructions needed to perform motion compensation on the PPG signals as described herein and to perform heart rate measurement based on the motion compensated PPG signals. Embodiments of motion compensation that may be executed by the MCU 308 are described in reference to FIGS. 4, 5, and 6. Memory 318 may be any suitable memory device or devices, such as, for example, one or more ferroelectric random access memory (FRAM) devices. Memory 318 is coupled to the MCU 308 and may be used, for example, to store data used in the execution of the heart rate monitoring and to store a heart rate history.

The IMU 312 is coupled to the MCU 308 via an interface provided by the MCU 308 and provides data regarding the motion of a person wearing the monitor device 300 to the MCU 308. More specifically, the IMU 312 includes a three axis accelerometer to provide the X-axis acceleration signal (accX), the Y-axis acceleration (accY) signal and the z-axis acceleration (accZ) signal to the MCU 308. The IMU 312 may be any suitable IMU device, such as, for example, an IMU device available from Invensense, Inc.

The Bluetooth transceiver 314 is coupled to the MCU 308 and may be used, for example, to transfer the computed heart rate measurement of a person wearing the monitor device 300 to another device for display and/or further processing. For example, the heart rate measurement may be transmitted to a smart phone or other personal digital assistant, a laptop computer, a desktop computer, a medical monitoring device, etc. The Bluetooth transceiver 314 may be any suitable Bluetooth device, such as, for example, a CC25xx Bluetooth system-on-a-chip (SOC) available from Texas Instruments, Inc.

The USB (universal serial bus) transceiver 316 is coupled to the MCU 308 and may be used, for example, to transfer the computed heart rate measurement of a person wearing the monitor device 300 to another device for display and/or further processing. For example, the heart rate measurement may be transmitted to a smart phone or other personal digital assistant, a laptop computer, a desktop computer, a medical monitoring device, etc. The associated USB port may also be used to charge a battery (not shown) in the monitor device 300.

The AFE 310 is coupled to the MCU 308 and the PPG sensor component 304 and provides a control interface between the MCU 308 and PPG sensor component 304. The AFE 310 includes functionality to receive a PPG signal from the PPG sensor component 304, convert the signal to a digital signal, apply analog signal conditioning such as changing the gain of the signal, and provide the digital PPG signal to the MCU 308 for heart rate measurement. The AFE 310 also includes functionality to drive current to one or more LEDs in the PPG sensor 304 as directed by the MCU 308. The particular current to be used and the timing of when to apply the current may be controlled by the MCU 308. The AFE 310 may be any suitable AFE device, such as, for example, the AFE4400 provided by Texas Instruments, Inc.

In some embodiments, the PPG heart rate monitor device 300 includes a display component (not shown) coupled to the MCU 308. The display component may be used to display the heart rate of a person wearing the monitor device 300.

Figure 4:
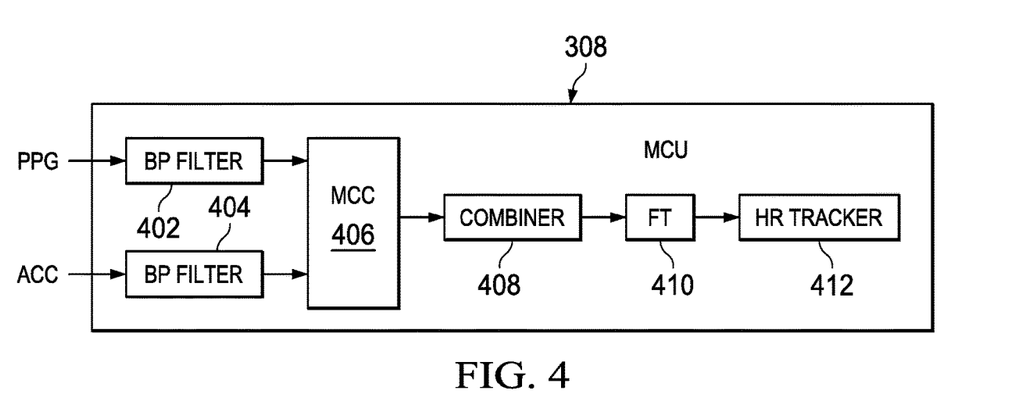
FIG. 4 and FIG. 5 are block diagrams illustrating an embodiment of motion compensation of a PPG signal and heart rate tracking that may be performed in a suitably configured heart rate monitor device such as that of FIG. 3.
Figure 5:
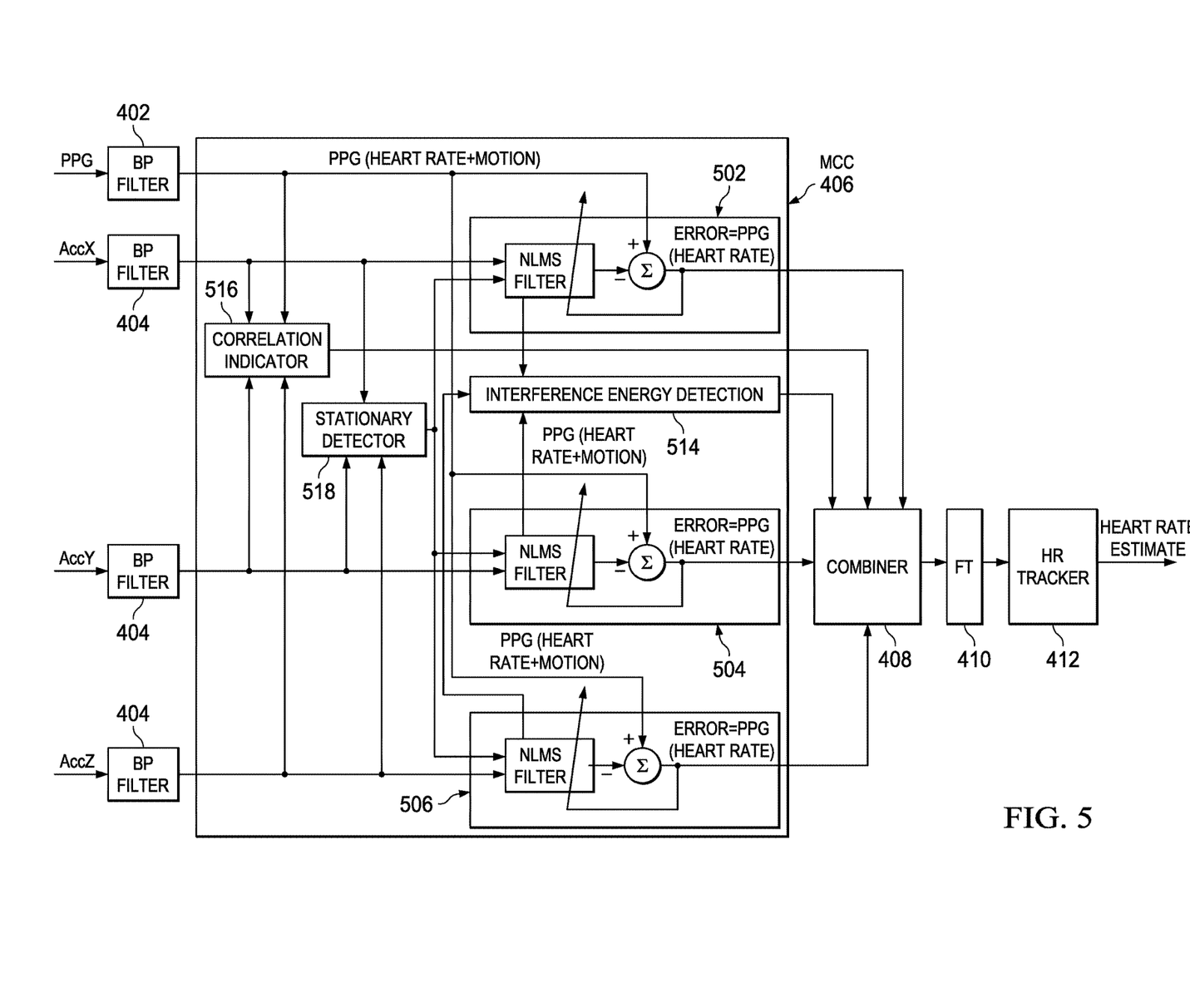

FIG. 4 and FIG. 5 are block diagrams illustrating an embodiment of motion compensation of a PPG signal and heart rate tracking that may be performed in a suitably configured heart rate monitor device, such as, for example, the heart rate monitor device 300 of FIG. 3. Embodiments are described in reference to heart rate monitor device 300 for simplicity of explanation. One of ordinary skill in the art will understand embodiments for other hardware architectures. Further, embodiments are described assuming the various components are implemented as software executed by a processor such as the MCU 308. One of ordinary skill in the art will understand embodiments in which one or more of the components may be implemented in hardware. For example, the FT component 410 may be an FFT hardware accelerator tightly coupled with the central processing unit of the MCU 308. In another example, one or more of the components may be implemented in an application specific integrated circuit (ASIC).

Referring first to FIG. 4, the bandpass filter 402 receives the PPG signal from the AFE 310 is filtered 402 and outputs a filtered PPG signal. The bandpass filter 404 receives the X-axis acceleration signal (accX), the Y-axis acceleration signal (accY) and the z-axis acceleration signal (accZ) from the IMU 312 and output filtered versions of these acceleration signals. The bandpass filters 402, 404 are filters with the same in-band and out-of-band characteristics.

The motion compensation component (MCC) 406 receives the filtered PPG signal and the filtered acceleration signals and performs motion compensation on the PPG signal based on the acceleration signals. More specifically, the MCC 406 performs motion compensation on the PPG signal with respect to each of the acceleration signals and generates three output signals, $PPG_{accX}$, $PPG_{accY}$, and $PPG_{accZ}$. The motion compensation is described in more detail in reference to FIG. 5. In some embodiments, the MCC 406 also outputs weighting data that may be used by the combiner 408 to determine weights for combining the three motion filtered PPG signals, e.g., indications of the correlation of the PPG signal with each acceleration signal and/or the predicted interference energy removed from the PPG signal to generate each of the signals output by the MCC 406.

The combiner 408 combines the three signals output by the MCC 406 as per $$a*PPG_{accX}+b*PPG_{accY}+c*PPG_{accZ}$$

to generate the final motion compensated PPG signal. Further, the combiner 408 may determine the values of the weights as per one of the approaches previously described herein based on weighting data from the MCC 406 or the weights may all have the same value, i.e., a=b=c=K where K is a predetermined constant. In some embodiments, K=1.

The FT component 410 applies an FFT to the final motion compensated PPG signal to convert the signal from the time domain to the frequency domain. The resulting signal is then provided to the heart rate tracker 412 to be used for heart rate estimation.

The block diagram of FIG. 5 illustrates an embodiment of the motion compensation performed by the MCC 406. The correlation indicator component 516 receives the filtered PPG signal and the filtered acceleration signals and generates weighting data for the combiner 408 that is indicative of the correlation between the PPG signal and each of the acceleration signals. That is, the correlation indicator component 516 computes the correlation coefficients between each acceleration signal and the PPG signal in T second window. Computation of correlation coefficients is previously described herein.

In some embodiments, the output of the correlation indicator component 516 is the correlation coefficients for each combination of PPG signal and acceleration signal and the combiner 408 uses the correlation coefficients to determine the weight values used to combine the motion compensated PPG signals $PPG_{accX}$, $PPG_{accY}$, and $PPG_{accZ}$. In some embodiments, the output of the correlation indicator component 516 is the maximum of the correlation coefficients for each combination of PPG signal and acceleration signal and the combiner 408 uses the maximum coefficients to determine the weight values. Computation of the maximum of the correlation coefficients is previously described herein.

The interference energy detection component 514 receives the filtered PPG signal, the filtered acceleration signals, and the current filter coefficients from each adaptive filter 502, 504, 506 and generates weighting data for the combiner 408 that is indicative of the predicted interference energy removed from the PPG signal by each adaptive filter 502, 504, 506. That is, the interference energy detection component 514 computes the predicted interference energy removed from the PPG signal by each adaptive filter 502, 504, 506 in T second window. Computation of predicted interference energy is previously described herein.

The stationary detector component 518 receives the filtered acceleration signals and generates an indication of whether or not the person wearing the monitor device 300 is stationary, i.e., a stationary indicator. The stationary detector component 518 may use any suitable technique to determine if the person is in motion. An example of one such suitable technique is previously described herein.

The adaptive filters 502, 504, 506 each receive the filtered PPG signal and a respective acceleration signal accX, accY, accZ and output respective motion compensated PPG signals $PPG_{accX}$, $PPG_{accY}$, and $PPG_{accZ}$. In this embodiment, each adaptive filter 502, 504, 506 is a normalized least mean squares (NLMS) filter in which the input signal is the PPG signal and the reference signal is the respective acceleration signal. As is well known by those of ordinary skill in the art, an NLMS filter is a variant of a least mean squares (LMS) filter which is a class of adaptive filter used to mimic a desired filter by finding the filter coefficients that relate to producing the least mean squares of the error signal, i.e., the difference between the desired signal and the actual signal. As previously mentioned herein, other adaptive filters may be used, such as, for example recursive least squares (RLS) filters.

The adaptive filters 502, 504, 506 also receive the stationary indicator from the stationary detector component 518. If the stationary indicator indicates that the person is stationary, the adaptive filters 502, 504, 506 do not filter the input PPG signal and the output of each adaptive filter is the input PPG signal. Further, the combiner 408 performs no combining and passes one of the input PPG signals as the output PPG signal. In some embodiments, if the stationary indicator indicates that the person is stationary, the weights of the adaptive filter are not changed, i.e., the weights remain at their current values. Thus, the filter weights are only updated when the person is in motion. In some embodiments, if the stationary indicator indicates that the person is stationary, the weights of the adaptive filter are reset to their initial values.

FIG. 5 includes both a correlation indicator component 516 and an interference energy detection component 514 for ease of description. One of ordinary skill in the art will understand embodiments in which one of these components is not present or is otherwise not used. Further, one of ordinary skill in the art will understand embodiments in which neither component is present, e.g., in embodiments in which the combiner uses a weighting scheme in which the weight values are constants.

Figure 6:
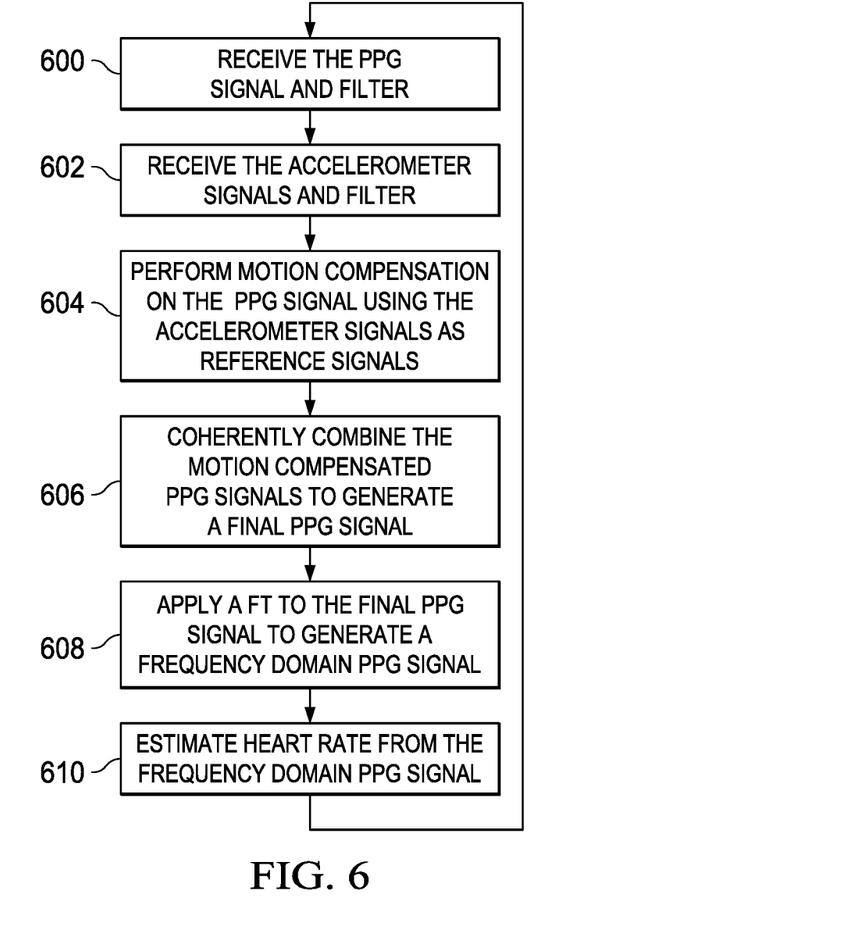
FIG. 6 is a flow diagram of a method for motion compensation of a PPG signal and heart rate tracking that may be performed in a suitably configured heart rate monitor device such as that of FIG. 3.

FIG. 6 is a flow diagram of a method for motion compensation of a PPG signal and heart rate tracking that may be performed in a suitably configured heart rate monitor device, such as, for example, the heart rate monitor device 300 of FIG. 3. Embodiments are described in reference to heart rate monitor device 300 for simplicity of explanation. One of ordinary skill in the art will understand embodiments for other hardware architectures. The method may be performed continuously while the heart rate monitor device is turned on.

A PPG signal is received 600 by the MCU 308 from the PPG sensor component 304 via the AFE 310 and is filtered using a bandpass filter. Accelerometer signals, i.e., an X-axis acceleration signal, a Y-axis acceleration signal, and a Z-axis acceleration signal are also received 602 by the MCU 308 from the IMU 312 and are filtered using a bandpass filter. Motion compensation is then performed 604 on the filtered PPG signal using the filtered acceleration signals as reference signals to generate three motion compensated PPG signals. More specifically, the filtered PPG signal is adaptively filtered using each of the X-axis acceleration signal, the Y-axis acceleration signal, and the Z-axis acceleration signal as a reference signal to generate three motion compensated PPG signals. The adaptive filter may be, for example, an NLMS filter or an RLS filter.

The three motion compensated PPG signals are then coherently combined 606 as per $$a*PPG_{accX}+b*PPG_{accY}+c*PPG_{accZ}$$

to generate a final motion compensated PPG signal. The values of the weights may be determined as per one of the approaches previously described herein or the weights may all have the same value, i.e., a=b=c=K where K is a predetermined constant. In some embodiments, K=1.

A single FT is then applied 608 to the final motion compensated PPG signal to generate a frequency domain PPG signal. The frequency domain signal is then used to estimate 610 the heart rate.

In some embodiments, a determination is also made as to whether or not the user of the heart rate monitor device is stationary or in motion. Any suitable technique may be used to make this determination. One such suitable technique is previously described herein. If the user is stationary, the PPG signal is not adaptively filtered. In some embodiments, the weights of the adaptive filters remain unchanged if the user is stationary. In some embodiments, the weights of the adaptive filters are reset to initial values if the user is stationary.

OTHER EMBODIMENTS

While the invention has been described with respect to a limited number of embodiments, those skilled in the art, having benefit of this disclosure, will appreciate that other embodiments can be devised which do not depart from the scope of the invention as disclosed herein.

For example, one of ordinary skill in the art will understand that embodiments of may be used in PPG heart rate monitor devices housed in form factors suitable for monitoring heart rate in various locations on the body of a person such as, for example, the forehead, an ear lobe, a finger, an upper arm, a wrist, or a chest.

In another example, one of ordinary skill in the art will understand embodiments in which the filtered PPG signal and the filtered acceleration signals are downsampled prior to further processing.

In another example, one of ordinary skill in the art will understand embodiments in which the stationary detector component is not present and the IMU determines whether the person is in motion and generates the value of the stationary indicator.

In another example, while some embodiments have been described herein assuming an FFT is used, one of ordinary skill in the art will understand embodiments in which other suitable Fourier Transforms are used.

The methods described herein may be implemented in hardware, software, firmware, or any combination thereof. If completely or partially implemented in software, the software may be executed in one or more processors, such as a microcontroller, microprocessor, application specific integrated circuit (ASIC), field programmable gate array (FPGA), or digital signal processor (DSP). The software instructions may be initially stored in a computer-readable medium and loaded and executed in the processor. In some cases, the software instructions may also be sold in a computer program product, which includes the computer-readable medium and packaging materials for the computer-readable medium. In some cases, the software instructions may be distributed via removable computer readable media, via a transmission path from computer readable media on another digital system, etc. Examples of computer-readable media include non-writable storage media such as read-only memory devices, writable storage media such as disks, flash memory, memory, or a combination thereof.

Although method steps may be presented and described herein in a sequential fashion, one or more of the steps shown in the figures and described herein may be performed concurrently, may be combined, and/or may be performed in a different order than the order shown in the figures and/or described herein. Accordingly, embodiments should not be considered limited to the specific ordering of steps shown in the figures and/or described herein.

It is therefore contemplated that the appended claims will cover any such modifications of the embodiments as fall within the true scope of the invention.

What is claimed is:

1. A method for heart rate measurement in a photoplethysmograph (PPG) heart rate monitor device, the method comprising:
    receiving a PPG signal from a PPG sensor of the heart rate monitor device;
    receiving an X-axis acceleration signal, a Y-axis acceleration signal, and a Z-axis acceleration signal from an accelerometer of the heart rate monitor device;
    performing motion compensation on the PPG signal, wherein a first motion compensated PPG signal is generated with reference to the X-axis acceleration signal, a second motion compensated PPG signal is generated with reference to the Y-axis acceleration signal, and a third motion compensated PPG signal is generated with reference to the Z-axis acceleration signal;
    combining the first motion compensated PPG signal, the second motion compensated PPG signal, and the third motion compensated PPG signal to generate a fourth motion compensated PPG signal, wherein a first weight is applied to the first motion compensated PPG, a second weight is applied to the second motion compensated PPG signal, and a third weight is applied to the third motion compensated PPG signal;
    performing a single Fourier Transform (FT) on the fourth motion compensated PPG signal to generate a frequency domain PPG signal; and
    estimating a heart rate based on the frequency domain PPG signal.

2. The method of claim 1, wherein the first motion compensated PPG signal is generated by applying a first adaptive filter to the PPG signal with the X-axis acceleration signal as a reference signal, the second motion compensated PPG signal is generated by applying a second adaptive filter to the PPG signal with the Y-axis acceleration signal as a reference signal, and the third motion compensated PPG signal is generated by applying a third adaptive filter to the PPG signal with the Z-axis acceleration signal as a reference signal.

3. The method of claim 2, wherein the first adaptive filter, the second adaptive filter, and the third adaptive filter are a same filter type, the filter type selected from one of a normalized least mean squares (NLMS) filter and a recursive least squares (RLS) filter.

4. The method of claim 2, wherein weights of the first adaptive filter, the second adaptive filter, and the third adaptive filter are updated only when a user of the heart rate monitor device is in motion.

5. The method of claim 2, wherein weights of the first adaptive filter, the second adaptive filter, and the third adaptive filter are reset to initial values when a user of the heart rate monitor device is stationary.

6. The method of claim 2, wherein a value of the first weight, a value of the second weight, and a value of the third weight are based on predicted interference energy removed from the PPG signal by the first adaptive filter, predicted interference energy removed from the PPG signal by the second adaptive filter, and predicted interference energy removed from the PPG signal by the third adaptive filter.

7. The method of claim 1, wherein the first weight, the second weight, and the third weight are equal.

8. The method of claim 1, wherein a value of the first weight, a value of the second weight, and a value of the third weight are based on an amount of correlation between the PPG signal and the X-axis acceleration signal, an amount of correlation between the PPG signal and Y-axis acceleration signal, and an amount of correlation between the PPG signal and the Z-axis acceleration signal.

9. A photoplethysmograph (PPG) heart rate monitor device comprising:
   a PPG sensor component configured to generate an analog PPG signal;
   an accelerometer configured to generate an X-axis acceleration signal, a Y-axis acceleration signal, and a Z-axis acceleration signal;
   a motion compensation component coupled to the PPG sensor to receive the PPG signal and coupled to the accelerometer to receive the X-axis acceleration signal, the Y-axis acceleration signal, and the Z-axis acceleration signal, wherein the motion compensation component is configured to generate a first motion compensated PPG signal with reference to the X-axis acceleration signal, a second motion compensated PPG signal with reference to the Y-axis acceleration signal, and a third motion compensated PPG signal with reference to the Z-axis acceleration signal;
      a combiner configured to combine the first motion compensated PPG signal, the second motion compensated PPG signal, and the third motion compensated PPG signal to generate a fourth motion compensated PPG signal, wherein a first weight is applied to the first motion compensated PPG, a second weight is applied to the second motion compensated PPG signal, and a third weight is applied to the third motion compensated PPG signal; and
      a Fourier Transform (FT) component configured to perform a single FT on the fourth motion compensated PPG signal to generate a frequency domain PPG signal for heart rate estimation.

10. The PPG heart rate monitor device of claim 9, wherein the motion compensation component comprises a first adaptive filter configured to generate the first motion compensated PPG signal using the X-axis acceleration signal as a reference signal, a second adaptive filter configured to generate the second motion compensated PPG signal using the Y-axis acceleration signal as a reference signal, and a third adaptive filter configured to generate the third motion compensated PPG signal using the Z-axis acceleration signal as a reference signal.

11. The PPG heart rate monitor device of claim 10, wherein the first adaptive filter, the second adaptive filter, and the third adaptive filter are a same filter type, the filter type selected from one of a normalized least mean squares (NLMS) filter and a recursive least squares (RLS) filter.

12. The PPG heart rate monitor device of claim 10, wherein weights of the first adaptive filter, the second adaptive filter, and the third adaptive filter are updated only when a user of the heart rate monitor device is in motion.

13. The PPG heart rate monitor device of claim 10, wherein weights of the first adaptive filter, the second adaptive filter, and the third adaptive filter are reset to initial values when a user of the heart rate monitor device is stationary.

14. The PPG heart rate monitor device of claim 10, wherein a value of the first weight, a value of the second weight, and a value of the third weight are based on predicted interference energy removed from the PPG signal by the first adaptive filter, predicted interference energy removed from the PPG signal by the second adaptive filter, and predicted interference energy removed from the PPG signal by the third adaptive filter.

15. The PPG heart rate monitor device of claim 9, wherein the first weight, the second weight, and the third weight are equal.

16. The PPG heart rate monitor device of claim 9, wherein a value of the first weight, a value of the second weight, and a value of the third weight are based on an amount of correlation between the PPG signal and the X-axis acceleration signal, an amount of correlation between the PPG signal and Y-axis acceleration signal, and an amount of correlation between the PPG signal and the Z-axis acceleration signal.

* * * * *